United States Patent
Mueller-Hartmann et al.

(10) Patent No.: US 9,624,486 B2
(45) Date of Patent: Apr. 18, 2017

(54) METHOD AND ELECTRODE ASSEMBLY FOR TREATING ADHERENT CELLS

(75) Inventors: Herbert Mueller-Hartmann, Cologne (DE); Andreas Wirth, Teufen (CH)

(73) Assignee: LONZA COLOGNE GMBH, Cologne (DE)

(*) Notice: Subject to any disclaimer, the term of this patent is extended or adjusted under 35 U.S.C. 154(b) by 159 days.

(21) Appl. No.: 13/806,491

(22) PCT Filed: Jun. 21, 2011

(86) PCT No.: PCT/EP2011/060312
§ 371 (c)(1),
(2), (4) Date: Jun. 14, 2013

(87) PCT Pub. No.: WO2011/161092
PCT Pub. Date: Dec. 29, 2011

(65) Prior Publication Data
US 2013/0260434 A1 Oct. 3, 2013

(30) Foreign Application Priority Data

Jun. 22, 2010 (EP) .................................... 10006458

(51) Int. Cl.
*C12N 13/00* (2006.01)
*C12M 1/32* (2006.01)
(Continued)

(52) U.S. Cl.
CPC ............. *C12N 13/00* (2013.01); *C12M 23/12* (2013.01); *C12M 35/02* (2013.01); *C12N 15/87* (2013.01); *A61N 1/327* (2013.01)

(58) Field of Classification Search
None
See application file for complete search history.

(56) References Cited

U.S. PATENT DOCUMENTS 5,134,070 A   7/1992  Casnig
5,273,525 A * 12/1993  Hofmann ................. 604/21
(Continued)

FOREIGN PATENT DOCUMENTS

CN    1889886 A    1/2007
CN    1930280 A    3/2007
(Continued)

OTHER PUBLICATIONS

NPL pdf "CUY900-13-3-5 Technical_Drawings" of webpage at http://www.sonidel.com/sonidel/%20cuy900-13-3-5_technical_drawings/ accessed Jun. 13, 2014.*
(Continued)

*Primary Examiner* — Ralph Gitomer
*Assistant Examiner* — Trent Clarke
(74) *Attorney, Agent, or Firm* — Joyce von Natzmer; Agris & von Natzmer LLP

(57) ABSTRACT

The invention relates to an electrode assembly 20, in particular for applying at least one electric field to adherent cells, comprising at least two electrodes 21, each having at least one surface 32 which is arranged opposite the corresponding surface 32 of the other electrode 21, wherein an electrically insulating material 26 is arranged at least partially between the surfaces 32 of the electrodes 21. The solution according to the invention allows the electric field to be concentrated in the region of the cells to be treated such that a voltage pulse, or the current produced thereby, flows through the cells without the majority flowing away over the cells unused in the electrolyte. The invention further relates to a method for applying at least one electric field to adherent cells, in which the electric field is generated by applying a voltage to at least two electrodes, the electric field is concentrated on the side of the electrodes which faces the
(Continued)

cells and/or is limited to the space between the cells and the side of the electrodes which faces the cells.

21 Claims, 8 Drawing Sheets

(51) Int. Cl.
*C12M 1/42* (2006.01)
*C12N 15/87* (2006.01)
*A61N 1/32* (2006.01)

(56) References Cited

U.S. PATENT DOCUMENTS

| | | | |
|---|---|---|---|
| 5,869,326 | A | 2/1999 | Hofmann |
| 6,352,853 | B1 | 3/2002 | King et al. |
| 7,062,310 | B2 | 6/2006 | Bernhart et al. |
| 8,101,401 | B2 | 1/2012 | Muller-Hartmann et al. |
| 8,994,382 | B2 | 3/2015 | Nielsen et al. |
| 2002/0164776 | A1 | 11/2002 | Beichmann et al. |
| 2003/0157708 | A1 | 8/2003 | Ozaki |
| 2005/0089991 | A1 | 4/2005 | Walters et al. |
| 2007/0105214 | A1 | 5/2007 | Micklash et al. |
| 2009/0305380 | A1 | 12/2009 | Ragsdale |
| 2010/0021038 | A1 | 1/2010 | Schulz |
| 2010/0249771 | A1 | 9/2010 | Pearson et al. |

FOREIGN PATENT DOCUMENTS

| | | |
|---|---|---|
| CN | 101421913 A | 4/2009 |
| CN | 101558147 A | 10/2009 |
| JP | 1-112787 A | 5/1989 |
| JP | 1-235576 A | 9/1989 |
| JP | 2-131584 A | 5/1990 |
| JP | 10-234366 A | 9/1998 |
| JP | 2003-144136 A | 5/2003 |
| JP | 2004 202086 | 7/2004 |
| JP | 2005-261323 A | 9/2005 |
| JP | 2010022360 A | 2/2010 |
| WO | 00/23563 A1 | 4/2000 |
| WO | 2005/056788 A1 | 6/2005 |
| WO | 2007094947 A2 | 8/2007 |
| WO | 2008/104086 A1 | 9/2008 |
| WO | 2009/131972 A1 | 10/2009 |
| WO | 2009/140161 A1 | 11/2009 |

OTHER PUBLICATIONS

NPL pdf "nepagene electrodes" of webpage at http://www.bulldog-bio.com/nepagene/Electrodes.pdf accessed Jun. 13, 2014.*
NPL pdf "BTX Petri Pulser" of webpage at http://www.btxonline.com/petri-dish-electrode/ accessed Jun. 13, 2014.*
NPL pdf document "JP 2004-202086 Japanese Patent Office English machine translation" downloaded from Japanese Patent Office at http://www4.ipdl.inpit.go.jp/Tokujitu/tjsogodbenk.ipdl; accessed Jun. 13, 2014.*
Database WPI Week 200449, Abstract XP002610220, Thomson Scientific, London, GB; AN 2004-514495 (Jul. 22, 2004).
"Petri Pulser Electrode Users Manual," BTX Harvard Apparatus, retrieved Mar. 26, 2013, at http://www.btxonline.com/content/PDFS/UserManuals/Petri_Pulser_Electrodes_0908.pdf (closest found to catalog found Nov. 2010).
Lin, Y.C. et al., "Simulation and experimental demonstration of the electric field assisted electroporation microchip for in vitro gene delivery enhancement." Lab Chip (2004) vol. 4, pp. 104-108.
English Translation of First Office Action, dated Feb. 20, 2014, from the Chinese Intellectual Property Office in Related Chinese Application No. CN 201180030237.9.
English Translation of Second Office Action, dated Jan. 13, 2015, from the Chinese Intellectual Property Office in Related Chinese Application No. CN 201180030237.9.
English Translation of Notice of Reasons for Rejection, dated Mar. 10, 2015, from the Japan Patent Office in Related Japanese Application No. JP P2013-515857.
English Translation of First Office Action, dated Feb. 21, 2014, from the Chinese Intellectual Property Office in Related Chinese Application No. CN 201180030236.4.
English Translation of Second Office Action, dated Jan. 13, 2015, from the Chinese Intellectual Property Office in Related Chinese Application No. CN 201180030236.4.
English Translation of Notice of Reasons for Rejection, dated Mar. 31, 2015, from the Japan Patent Office in Related Japanese Application No. JP P2013-515866.

* cited by examiner a)

b)

a)

b)

METHOD AND ELECTRODE ASSEMBLY FOR TREATING ADHERENT CELLS

CROSS-REFERENCE TO RELATED APPLICATIONS

This is the U.S. national stage of International application PCT/EP2011/060312, filed Jun. 21, 2011 designating the United States claiming priority to European application EP 10006458.3, filed Jun. 22, 2010.

BACKGROUND

The invention relates to an electrode arrangement, in particular for applying at least one electric field to adherent cells, comprising at least two electrodes which each include at least one area being disposed face to face with the corresponding area of the respective other electrode. The invention further relates to a method for applying at least one electric field to adherent cells, in which the electric field is generated by applying a voltage to at least two electrodes.

PRIOR ART

Application of an electric field or voltage pulse to living cells, so called electroporation or electrotransfection, is practiced for years on cells in various states. As single cells in suspension in a buffer solution, at adherent state in a culture container, usually at the bottom of a plastic container, and in vivo where cells usually are embedded in a tissue assembly of an extracellular matrix. In principle in electroporation foreign molecules are introduced into the cell from a buffer solution, which is adapted to the cells, or a cell culture medium by applying a short-term current flow, whereby the cell membrane are made permeable for the foreign molecules due to the action of electric voltage pulses or the thereby resulting electric filed and current flow. The cell suspension are placed often in a so called cuvette, that is a narrow, open container, which sample chamber has two opposite, parallel electrodes in the side walls, which serve for applying electric voltage. By the temporary emerging "pores" in the cell membrane the biologically active molecules first reach the cytoplasm, where the molecules possibly already are able to perform their function of interest and then under certain conditions as well the nucleus. Due to short-term application of a strong electric field, that is a short voltage pulse of a high current density, in addition cells, cell derivatives, subcellular particles and/or vesicles may also be fused. In the so called electrofusion, for example, the cells first are brought into close membrane contact by an inhomogeneous alternating electric field. By subsequent application of an electric field pulse then interaction of membrane parts occur, which finally results in fusion. For electrofusion thereby comparable apparative devices as for the electroporation are applicable. Moreover living cells may be stimulated by electric field even in a manner changing their properties.

From WO 2005/056778 A1 for example a method for electroporation is known, in which cells are growing on a microporous membrane located between two parallel arranged electrode surfaces.

U.S. Pat. No. 5,134,070 describes applications and devices for electroporation of cells, which are growing on an electrically conductive surface, which serves as electrode. The culture container is covered from above with a plate-shaped counter electrode, whereby a gap is formed across that electric discharge is possible.

Moreover from WO 2008/104086 A1 a device is known, in which cells are growing on co-planar electrode surfaces. The electrical contact between the electrodes is established by the cell culture medium above the cells, whereby the two electrode regions are separated by an isolating barrier, but which nevertheless allows an electrolyte bridge between the electrodes. That for example can consist of indium tin oxide, which as a transparent semiconductor allows microscopic analyses of the cells.

From WO 2009/131972 A1 a device for electroporation of cells, which are growing adherent on a round disc-shaped plate, is known. The device exhibits two electrodes arranged parallel to each other, whereby one electrode is located on the concave surface of an external cylinder and the other electrode on the convex surface of an internal cylinder.

Moreover from US 2009/0305380 A1 a device for electroporation of cells, which are immobilized on a solid area, is known. The electric field, which is applied to the cells, is generated by an arrangement of electrode pairs, which are located lying closely next to each other on a surface above the solid area. The electrodes are formed by means of electric rails, which are plated on the surface.

Both electrodes of one electrode pair are thereby arranged as close to each other that not more than one single cell can be located within the smallest distance between both electrodes.

The company BTX distributes as PetriPulser® an arrangement of alternating poled plane-parallel electrode plates, which can be applied vertically on adherent growing cells in a culture container. Thereby the electrodes immerse into the culture supernatant, whereby the spaces between the individual electrode plates are filled with culture medium. A significant disadvantage of this arrangement is that a major part of the current leaks in the cell free culture medium above the cells. But this field is only effective at the border area on the bottom of the container, where the cells are located, so that unnecessary high currents have to be provided. Moreover, high mortality has to be assumed because of pH-value changes and high current. Furthermore, the power supply for long term voltage pulses has to be strong enough to provide those high currents and thus charges and powers. Moreover, a large volume has to be provided, which is suitable for electroporation and which comprises the substrate to be transfected at sufficiently high concentration, whereby the amount of the substrate is correspondingly higher as well.

DESCRIPTION OF THE INVENTION

The object of the invention is to provide an electrode arrangement and a method allowing an efficient treatment of adherent cells with an electric field without the need of too high current densities.

The problem is solved according to the invention by the type of electrode arrangement as initially mentioned, in which an electrically isolating material is at least partially disposed between the areas of the electrodes. By the use of the solution according to the invention it is achieved, that the electric field can be concentrated in the region of cells to be treated, thus a voltage pulse or the hereby resulting current passing through the cell, without that a main part thereof leaks unused in the electrolyte above the cells. Hereby on the one hand the device for pulse generation can be dimensioned economically and on the other hand significant changes of the pH values can be avoided, which otherwise would result from high passing charge volumes caused by electrolysis. Moreover, the device according to the invention ensures that a spatially well distributed electric treatment across the culture area is carried out and areas with not treated cells are minimized. Thereby the percentage of successfully treated (for example transfected) cells and the survival rate as well as, by using DNA or mRNA, the expression level per cell are comparable to the corresponding values from electroporation of cells in suspension. By means of the inventive electrode arrangement thus thereby an efficient treatment of adherent cells with an electric field is allowed.

In advantageous embodiment of the electrode arrangement according to the invention it is intended, that at least three, preferably at least 4 or 5, in particular 6 to 12, electrodes are provided.

If the electrodes are formed like a plate or pin, as many electrodes as possible can be arranged in confined spaces, thus a particularly homogenous electric field can be generated. Thus, in an alternative embodiment of the invention, plate electrodes can be replaced by rows of metal pins. If these rows of electrically connected pins are arranged sufficiently close, they can replace continuous plate electrodes in respect of the generated electric field. "Sufficiently close" means in this context, that the distance between adjacent pins with identical polarity is less or at a maximum equal to the distance between the rows of pins with opposing polarity. The application of those arrangement is particularly advantageous, because the manufacture of electrode arrangements by insertion of metal pins or wires respectively pieces of wires into an injection moulding tool and subsequent encapsulation, for example with thermoplastic polymer, is widespread and therefore the manufacturing process can be easily controlled by many producers.

In further advantageous embodiment according to the electrode arrangement of the invention it is intended, that the areas are lateral surfaces of electrode plates that are disposed plane-parallel.

Preferably the areas may be completely separated from each other by the isolating material. That is achieved in a favorable way, preferably in that the space between the electrodes defined by the areas of the electrodes is completely filled with the isolating material.

In an advantageous embodiment of the invention, the isolating material is a thermoplastic polymer, preferably polyvinylchloride, polystyrene, polypropylene, polyethylene and/or polycarbonate. The electrodes are preferably made of metal and/or an electrically conductive synthetic material.

In advantageous embodiment of the electrode arrangement according to the invention, it is intended that the electrode arrangement includes at least one spacer at at least one side facing the cells, which avoids that the electrodes make direct contact with the cells. The one or more spacer ensures that a minimum distance between the electrodes and the cells is maintained and/or a defined distance between the electrodes and the cell can be adjusted.

In particularly advantageous embodiment of the electrode arrangement according to the invention it is intended, that the electrode arrangement is provided for insertion into at least one container being at least partially filled with a liquid, preferably a container having a bottom area to which living cells adhere, and that the isolating material displaces at least a part of the liquid upon insertion into the container. Thereby it is possible to bring the electrodes closely to the cells to be treated and to minimize the liquid located above the cells.

The electrodes are preferably at least partially disposed at the underside of a carrier. This carrier may be, for example, designed such that it can be inserted into or placed onto a reaction vessel so that the electrodes are exposed to the inner space of the reaction vessel. The reaction vessel may be thereby, for example, a single cuvette or a cell culture dish or preferably a part of a multi-well plate. The electrode arrangement according to the invention is used preferably for applying at least one electric field to adherent cells, in particular for electroporation of adherent cells, preferably in the form of at least one dipping electrode device. The electrode arrangement in the form of a dipping electrode device according to the invention allows in a favorable manner the transfection of adherent growing cells, whereby the electrode device is removable from the medium before and after transfection. Thereby easily maximum flexibility in accordance to the used cell culture system can be ensured, in particular the compatibility with as many culture systems as possible.

Moreover, the object according to the invention is achieved by a method as initially mentioned, in which the electric field is focused at the side of the electrodes facing the cells and/or restricted to the space between the cells and the side of the electrodes facing the cells. By means of this inventive solution it is achieved, that a voltage pulse or the hereby resulting current passes through the cells without that a main part thereof leaks unused in the electrolyte above the cells. Hereby on the one hand the device for pulse generation can be dimensioned economically and on the other hand significant changes of the pH values can be avoided, which otherwise would result from high passing charge volumes caused by electrolysis. Moreover, the device according to the invention ensures that a spatially well distributed transfection across the culture area is carried out and areas with non-transfected cells are minimized. Thereby the percentage of successfully transfected cells and the survival rate as well as, in case of using DNA, mRNA, siRNA or other expressible nucleic acids, the degree of influencing the expression per cell is comparable to the corresponding values from electroporation of cells in suspension. By means of the inventive method thereby an efficient treatment of adherent cells with an electric field is allowed.

In advantageous embodiment of the method according to the invention it is intended, that the electric field is restricted to the space between the cells and the exposed front side of the electrodes. Focusing and/or restricting the electric field is preferably achieved in that an electrically isolating material is placed between the electrodes.

In advantageous embodiment of the method according to the invention it is further intended, that an exposed front side of the electrodes is inserted into at least one container having a bottom area to which the cells adhere.

In particularly advantageous embodiment of the method according to the invention it is intended, that the effect of the electric field on the cells is optimized by adjusting the distance between the cells and the electrodes. In this way a sufficiently strong and homogenous electric field above the cells to be treated results, which in turn has a positive effect on the treatment efficiency. Thus, for example, transfection efficiency in electrotransfection of cells can be optimized by adjusting the distance between the electrodes and the cells.

In the following the invention is explained exemplarily in detail with reference to the figures.

DESCRIPTION OF EXEMPLARY AND PREFERRED EMBODIMENTS

Figure 1:
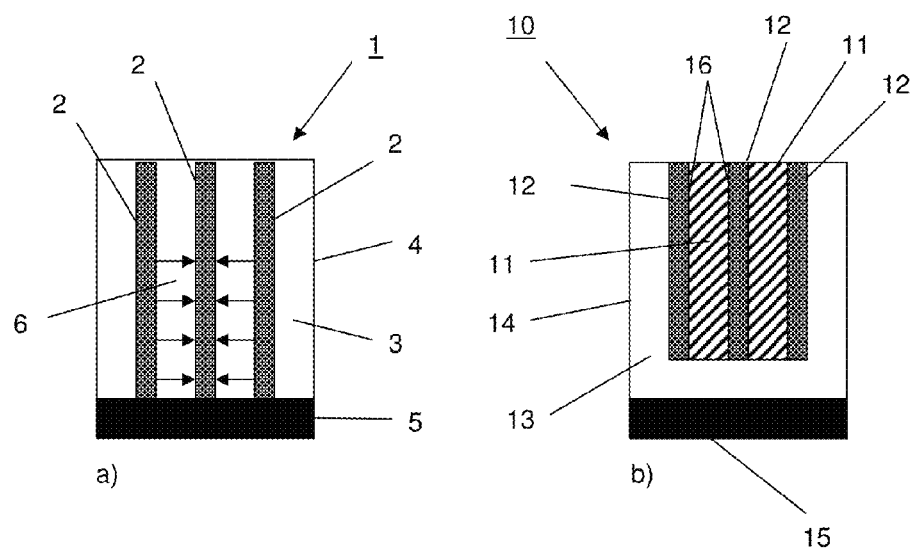
FIG. 1 shows (a) a schematic side view of an electrode arrangement according to prior art, (b) an exemplary schematic side view of an electrode arrangement according to the invention and (c) a schematic top view of a further exemplary embodiment of an electrode arrangement according to the invention.
Figure 1:
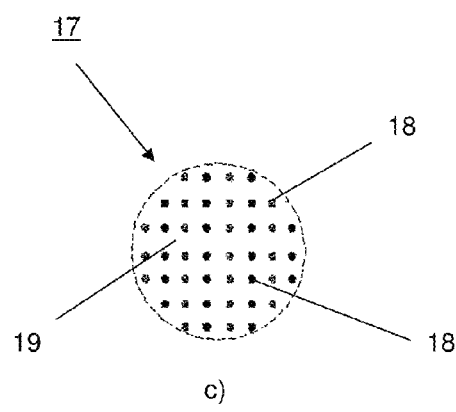

FIG. 1 shows (a) a schematic side view of an electrode arrangement 1 according to prior art with exposed electrodes 2 and (b) an exemplary schematic view of an electrode arrangement 10 according to the invention with electrical isolating material 11 between the electrodes 12. The electrode arrangement 1 according to prior art, which principally corresponds to PetriPulser® of BTX, consists of three plane-parallel arranged electrodes 2, which protrude into the inner space 3 of a container 4 and laying on the bottom area 5 of container 4 (FIG. 1a). On the bottom area 5 living cells are allowed to adhere and grow (adherent cells). The inner space 3 is filled with a liquid, for example a cell culture medium or another solution adapted to the cells, said solution fills the free space 6 between the electrodes 2 as well. Each electrode 2 is thus surrounded completely by the liquid. Because the liquid is electrically conductive, in case of applying a voltage at the electrodes 2 a major part of the current leaks in the liquid between the electrodes 2 (see arrow), thus in case of application of an non-permanent voltage source, that means for example by capacitor discharge, the voltage rapidly de-energizes and therefore the electric field is weakened over time. Only a part of the current is passing through the bottom area 5, so that biological effect of the current flow is poor.

The electrode arrangement according to the invention 10 comprises three plane-parallel arranged electrodes 12, which protrude into the inner space 13 of a container 14 (FIG. 1b). The container 14 comprises a bottom area 15 allowing living cells to adhere and grow (adherent cells). The inner space 13 is filled with a liquid, for example a cell culture medium or another liquid adapted to the cells. The space between the electrodes 12 is completely filled with an electrically isolating material 11, thus in case of applying a voltage at the electrodes 12 no current is allowed to leak in the space between the electrodes 12. The whole current is passing the space between the electrodes 12 and the bottom area 15, thus in case of applying a non-permanent voltage source (e.g. capacitor) the voltage drop takes longer and therefore the field strength for treatment of cells is increased over time. Thereby on the one hand the device for pulse generation can be dimensioned economically and on the other hand significant changes of pH values in the liquid can be avoided, which otherwise would be resulted from high voltage values passing caused by electrolytes.

According to the invention, for example, plane-parallel electrodes 12 can be separated by isolating material 11, thus electrically conductive surfaces of the electrodes 12 are only exposed downwards (towards the bottom area 15 or the cells adhered on it) and are in electrical contact with the environment. Due to full extension of the isolating material 11 in the region between each opposing arranged areas 16 of the plane-parallel electrodes 12, or at least in the area exposed to the liquid between the electrodes 12, where these show parallel lines, the electrical field can be focused or the current can be limited to the radius of action of interest. It is further a particular advantage that focusing of the electrical field in the region of the targeted cells or a limiting of the electrical current to the radius of action from now is possible by using of plane-parallel electrodes 12, which provide constant and more stable field strengths and current densities in the targeted region between the electrodes 12 and the bottom area 15. Suitable isolating materials therefore are for example plates or injected molding articles made of common, preferably thermoplastic synthetic materials, such as polyvinyl chloride, polystyrol, polypropylene, polyethylene or polycarbonate. By means of the arrangement according to the invention current leakage through the each opposing areas 16 of plane-parallel parts of the electrodes 12 can be avoided and thus voltage pulses of constant current are generated. Thus the arrangement according to the invention can be applied, for example per reaction depending on the area of the culture floor of cells to be treated, with one or more successive pulse discharges of low energy/currents to limit the necessary power per discharge.

For example an electrodes-isolator-sandwich can be used, in which the electrodes are poled alternating. In such an arrangement the field in the region below the active electrodes practically does not exist and therefore has no effect on cells located in the region below the active electrode. These regions are in close vicinity to an electrical conductor (the electrodes) and therefore outside of an appreciable field. Therefore the electrodes should be thin as possible (for example 50 pm) and approximately the entire cell-covered bottom area of the electrode arrangement should be covered with active regions of electrode-isolator combinations. Active regions are the areas below the isolating materials between opposing poled electrodes. Thereby in particular rounded geometries in cross section of the electrode arrangement are advantageous, which are of dimensions which would fit into the common cell culture container following the ANSI-SBS-Standard (American national standards institute—Society for Biomolecular Sciences).

FIG. 1c shows a schematic top view of the underside of a further exemplary embodiment of the electrode arrangement 17 of the invention with pin-shaped electrodes 18. Because the electrodes 18 each have a rounded cross section, their practically each entire circumferential area comprises areas, which are arranged opposing to the corresponding areas of the other electrodes 18. In this embodiment the space between the pin-shaped electrodes 18 is therefore completely filled with an electrical isolating material 19, thus the face surfaces of electrodes 18 of the underside are exposed and in contact with the environment. Thus all electrodes 18 each are electrically isolated to each other on their entire circumferential area, thus no current is allowed to leak across the space between the electrodes 18. In the electrode arrangement 17 according to the invention again all the current is passing the space between the electrodes 18 and the (not seen in this figure) cells, thus by application of non-permanent voltage sources (e.g. capacitor) the voltage drop takes longer and therefore the field strength for the treatment of cells is very high over time.

Figure 2:
FIG. 2 shows fluorescence microscopic images of expression of green fluorescence protein (GFP) in HeLa-cells, which were treated (a) firstly with an electrode arrangement according to prior art and (b) secondly by means of an electrode arrangement according to the invention.
Figure 2:
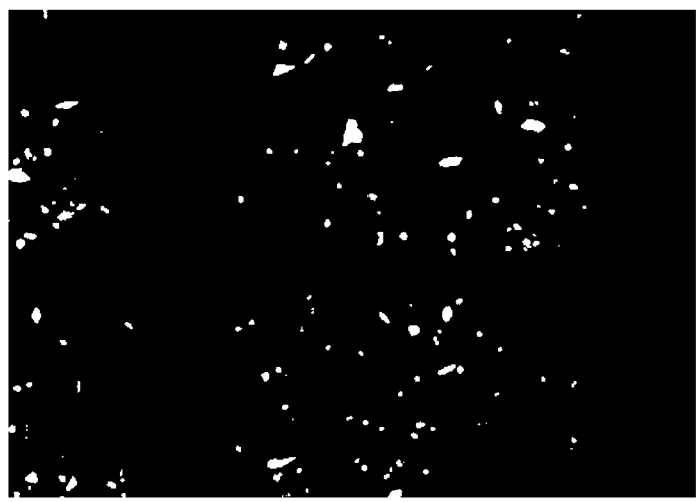

For experimental purpose a device or electrical arrangement according to the invention has been designed of alternating layers of aluminum films and 2 mm isolating material. The agglutinated device has been polished for adapting to the rounded geometries of the culture containers (6-well, 12-well, 24-well) and has been joined at the upper end by electrical contacts of every second electrode with two electrical connections. Subsequently, the device has been attached to a horizontal linear track or directly manually introduced into a culture well, in which adherent cells (here HeLa-cells) are growing. In this case to simplify matters the experimental device has been put on the culture floor, thus a distance of less than 1 mm between the cells and the electrode arrangement can be assumed. Previously the culture medium in the container had been replaced by 1 ml of a mixture of solutions (NUCLEOFECTOR Cell Line Solution R, Lonza) containing plasmid DNA (PMAXGFP, Lonza, 2 µg/100 µl). Then the alternating connected electrode films had been applied with different test pulses by means of NUCLEOFECTOR of Lonza, which values were in a range as used in applications with cuvettes of 100 µl volume. Subsequently the device has been removed again from the culture well and the electrolyte replaced again by medium to allow further cultivation of the cells. To simplify matters the solution-DNA mixture has been re-used in different wells. Analogous approach has been taken with the PETRIPULSER of BTX with the exception that because of the missing isolators between the electrodes 2 ml of the same solution-DNA mixture has been filled to achieve the same filling level. After one day the cells have been analyzed by means of flow cytometry. By application of the PETRIPULSER of BTX with approximately same electrode distance, hence same preconditions for the generation of electrical field, only very occasionally transfected cells are detectable (FIG. 21). Furthermore in this case error reports regarding over current shutdowns have been observed, which indicates that the PETRIPULSER is not suitable for the generation of sufficient high electrical fields, because of not limited current flow due to the open intermediary spaces between the electrode plates. In comparison by application of the inventive device 30% to 45% of the cells could be transfected (GFP expression, FIG. 2b). Thus it is evident that the inventive arrangement is able to transfect adherent cells efficiently.

Figure 3:
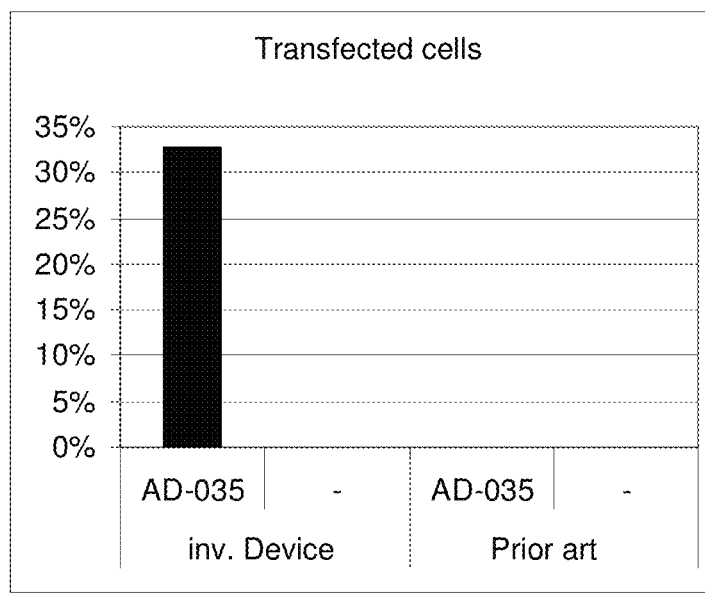
FIG. 3 shows bar diagrams of the comparison between an electrode arrangement according to prior art (Prior art) and an electrode arrangement according to the invention (inv. Device), whereby (a) on the one hand the portion of transfected cells and (b) on the other hand the survival rate of cells is depicted, each in percent (AD-035=Number of the electric parameters for adhered cells, NUCLEOFECTOR, Lonza).
Figure 3:
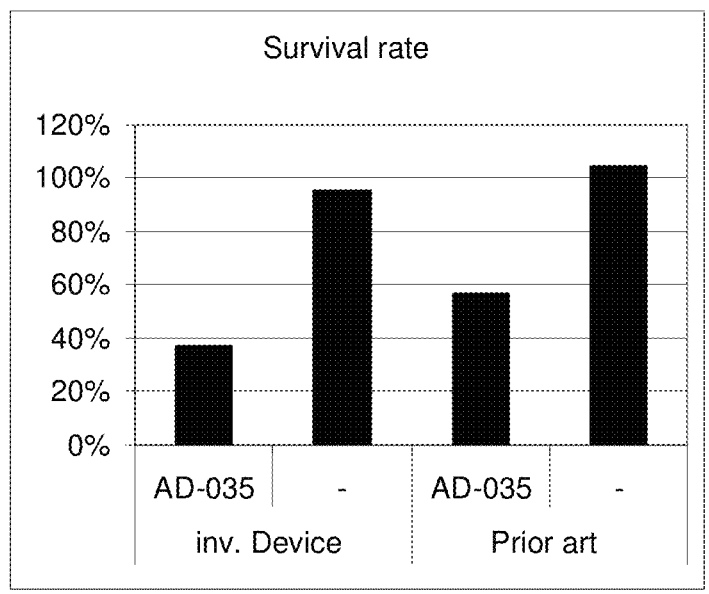

Subsequently cells were analyzed for survival, morphology and expression of the introduced genetic information. FIG. 3 shows a comparison of cells, which are transfected on the one hand with the inventive device described relating to FIG. 2b or on the other hand with the described method by means of the PETRIPULSER of BTX relating to FIG. 2b. It has been shown, that by means of the inventive electrode arrangement cells were transfected with high efficiency by maintaining high viability and morphological integrity (FIGS. 3a and 3b). The results provided scales in the same range as the comparative data of existing protocols for cells transfected in suspension. After treatment with PETRIPULSER indeed a higher survival rate has been determined but no significant transfection (FIGS. 3a and 3b).

Figure 4:
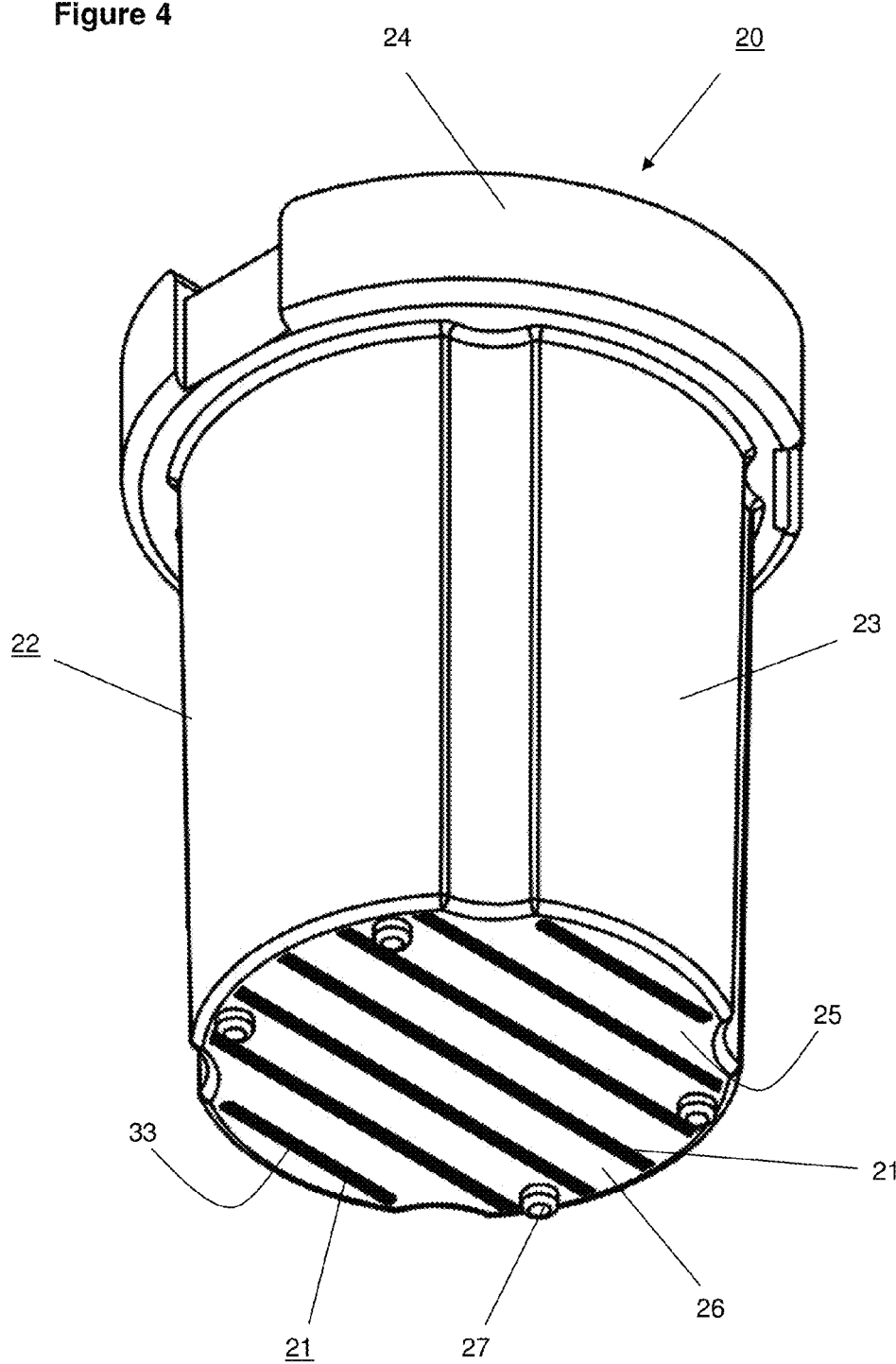
FIG. 4 shows a perspective view of the underside of an exemplary embodiment of an electrode arrangement according to the invention.

FIG. 4 shows a schematic view of the underside of exemplary embodiment of an electrode arrangement 20 according to the invention. The electrode arrangement 20 comprises seven electrodes 21, which are described hereafter in detail referring to FIGS. 5 and 7. The electrodes 21 are arranged in a carrier 22, which essentially is formed cylindrical. The carrier 22 comprises a base body 23 and a border area 24 at the upper end of the base body 23, whereby the outer diameter of the border area 24 is larger than the outer diameter of the base body 23, thus the border area 24 protrude outward of the base body 23. The electrodes 21 are arranged to a large extent within the base body 23 and are exposed with their lower face surface 33 at the underside 25 of the carrier 22, thus they are in contact with the environment. The single electrodes 21 are each electrically separated from each other by an isolating material 26, whereby in this embodiment the space between the single electrodes 26 is completely filled with the isolating material 26. The isolating material 26 between the opposing areas of the electrodes 21 ensures that when applying a voltage on the electrodes no current is allowed to leak across the space between the electrodes 21, if the electrodes are dipped in the electrically conductive liquid. The isolating material rather causes that when applying a voltage on the electrodes 21 current is passing through the face surface 33 of electrodes 21 and an electrical field is generated below the underside 25 of carrier 22. Because no significant current leaks across the space between the electrodes 21 voltage drop during discharge of a capacitor or another non-permanent voltage source takes longer, thus over time constant and more stable currents passing, which generate for most of the biological methods, for example transfection, a sufficiently strong electrical field over the period of discharge. The electrode arrangement 20 in particular is provided for insertion into a container at least partially filled with liquid, for example reaction vessel, a cell culture tray or a "well" of a multi-well-plate, whereby said container provides a bottom area, on which living cells are allowed to adhere. The adherent cells on the bottom area of the container are usually covered with a suitable liquid, for example a cell culture medium or a solution adapted to the desired electrical treatment, whereby the electrode arrangement 20 displaces at least a part of said liquid during insertion in the container. Thus the electrodes 21 with their face surfaces 33 are not lying directly on the bottom area of the container and thus not on the cells, the underside 25 of the carrier 22 provides four spacer 27, which ensure a sufficient distance between the electrodes 21 and the bottom area of the container.

Figure 5:
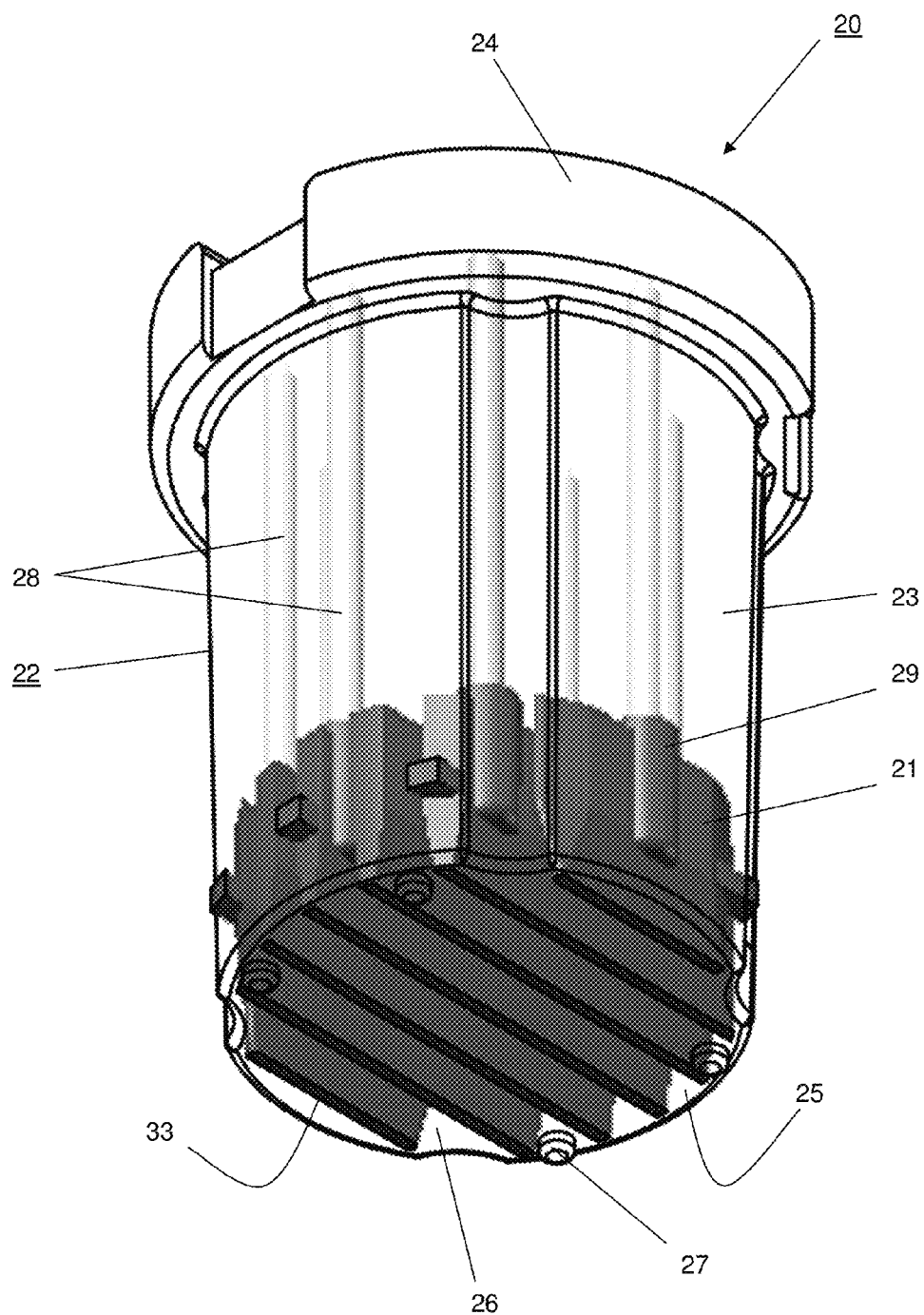
FIG. 5 shows a further perspective view of the electrode arrangement according to FIG. 4, whereby in this illustration the inner parts of the electrodes and contact elements are visible.

FIG. 5 shows a perspective view of the electrode arrangement 20 according to FIG. 4, whereby the internal parts of the electrode 21 are visibly shown in this depiction. It is clear form this depiction that the electrodes 21 in particular are formed plate-shaped, whereby the thickness of the electrode plates decreases towards the underside 25 of carrier 22. The exposed face surfaces 33 of the electrodes 21, which are in contact with the liquid in the container, are thus essentially thinner as the parts of the electrodes 21 placed within the base body 23. The advantage thereof is that the region below of each electrode 21 is minimized, within an effective electrical treatment of cells is not possible because of the too weak electrical field. In contrast at the opposing end, the electrodes 21 have to exhibit an increased thickness because these have to be efficiently contacted here for establishing a sufficient electrical contact. The electrical contact to each of the used voltage source is established in case of the present embodiment by pin-shaped contact elements 28, which are inserted into thicken areas 29 of the electrodes 21. The contact elements 28 are linked electrically with a voltage source each at its ends opposing to area 29 by means of a suitable contact device. The voltage source for example might be one or more capacitors, which allow controlled release of voltage pulses. The generated voltage pulses are forwarded to the electrodes 21 across the contact elements 28, thus at the underside of the electrodes 21, that means below the underside 25 of carrier 22, an electrical field is established, which because of the isolating material 26 between the electrodes is limited or focused on the space between the cells and the cell facing side of electrodes 21.

The electrode arrangement 20 according to the invention is manufactured preferably by an injection moulding process. Thereby first the contact elements 28 are inserted into a suitable injection moulding tool and then encapsulated with an electrically isolating polymer. In a second step then an electrically conductive polymer is injected, which form the electrodes 21. Alternatively the electrodes can be made of metal, preferably aluminum. In this embodiment first the metal electrodes are inserted into the injection moulding tool and then encapsulated with an electrically isolating polymer. In this embodiment the metal electrodes provide preferably upwards outstanding appendixes, which are suitable for contacting the electrodes electrically.

Figure 6:
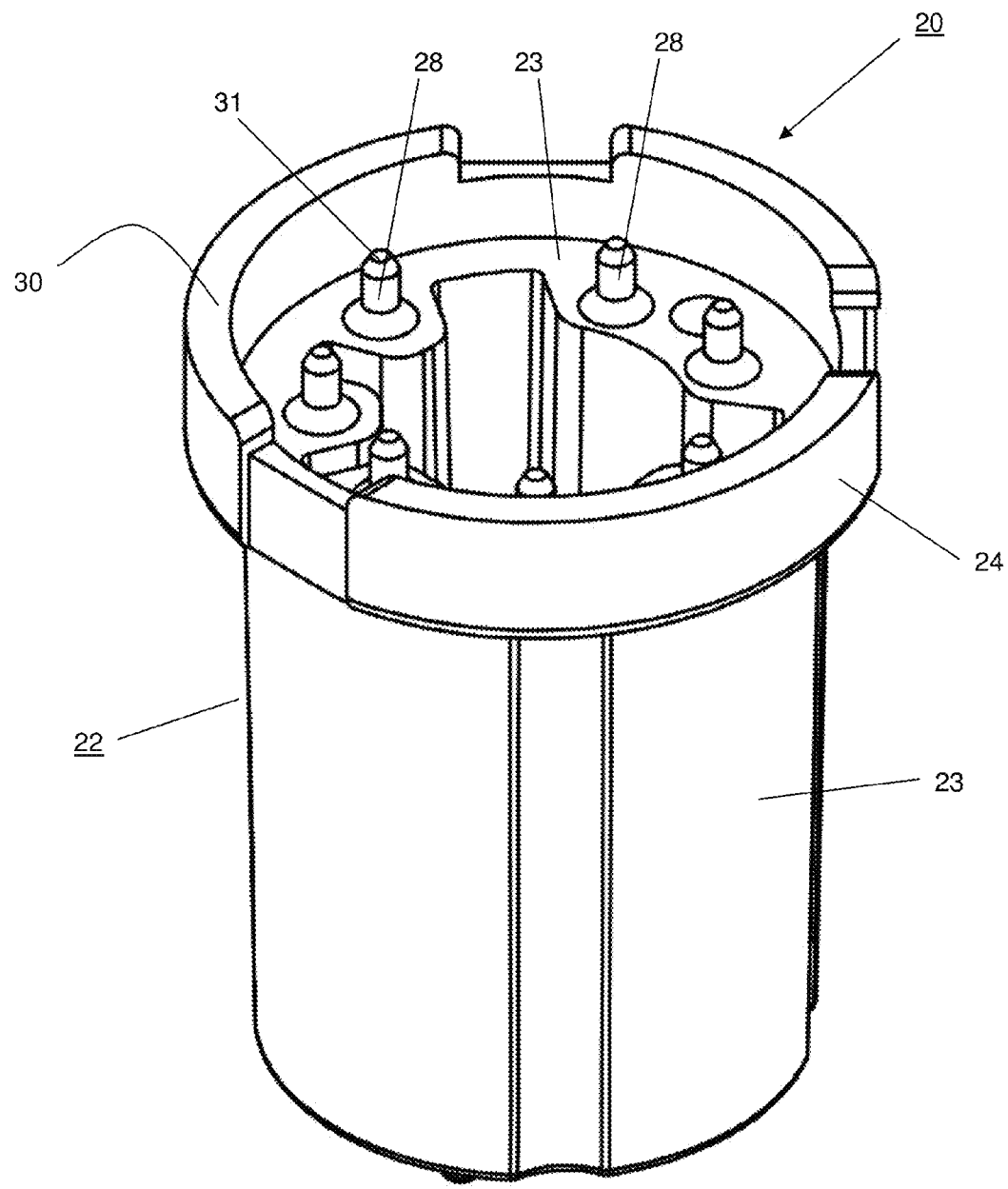
FIG. 6 shows a perspective view of the upper side of the electrode arrangement according to FIG. 4.

FIG. 6 shows a perspective view of the upper side 30 of the electrode arrangement 20 according to the invention relating to FIG. 4. It is clear thereof, that the contact elements 28 are outstanding upwards from the base body 23. Thus the contact elements 28 are completely surrounded with the electrically isolating material of the base body with the exception of the exposed ends 31. Using these exposed ends 31 the contact elements 28 can be electrically contacted by means of a suitable device to a voltage source.

Figure 7:
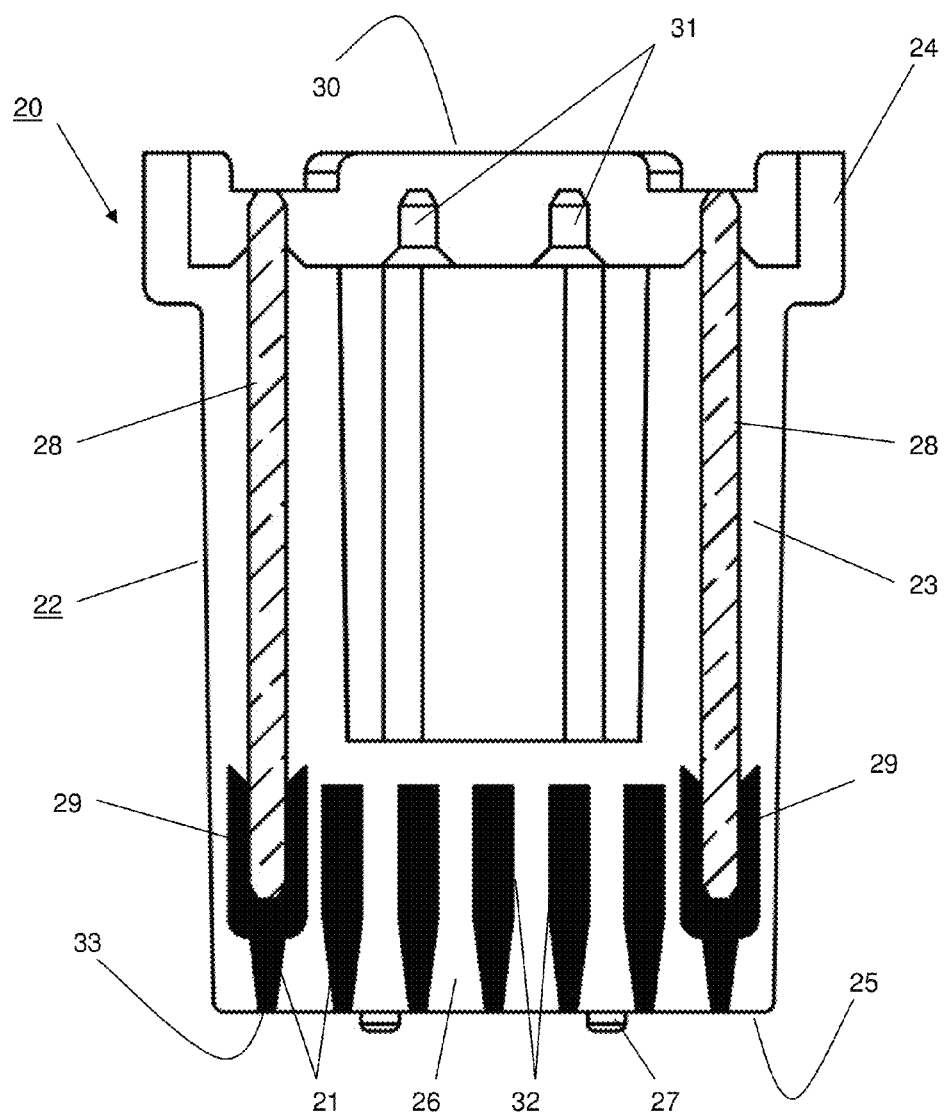
FIG. 7 shows a longitudinal section through the electrode arrangement according to FIGS. 4 to 6.

FIG. 7 shows a longitudinal section across the electrode arrangement 20 relating to FIGS. 4 to 6. From this depiction it is clear, that the diameter of the electrodes 21 tapers towards the underside 25 of the base body 23, thus the area below the electrodes 21, within the insufficient electrical field establishes, is minimized. At the opposing end of the electrodes 21 there is the area 29 with the increased thickness, in which contact elements 28 are inserted or injected respectively. This particular advantageous embodiment ensure a sufficient electrical contact between the contact elements 28 and the electrodes 21, thus an effective forwarding of voltage pulses from the voltage source until the electrodes 21 is ensured. If the electrode arrangement 20 is inserted into a container filled with liquid, on which bottom area living cells are adhered, the spacer 27 make sure, that the optimal distance between the underside of the electrodes 21 and the cells to be treated is set. Because the space between the each opposing arranged areas 32 of the electrodes 21 are completely filled with the isolating material 26, no liquid gets between the areas 32 of the electrodes 21, thus no current is allowed to leak through the region between the areas 32 of electrodes 21. In this way via application a voltage on the electrodes 21 the electrical field is concentrated at the cell facing side of the electrodes and limited or focused on the space between the cells and the electrodes 21. In this way cells can be treated very effectively and with relatively low demand of power. A further advantage of the invention is, that the electrode arrangement 20 displaces a part of the liquid during insertion into the container, because there are no intermediary spaces between the electrodes 21. Because of this reason the container have to be filled only with a small liquid amount, whereby solutions and substances necessary for the treatment can be saved and thus costs can be reduced.

Figure 8:
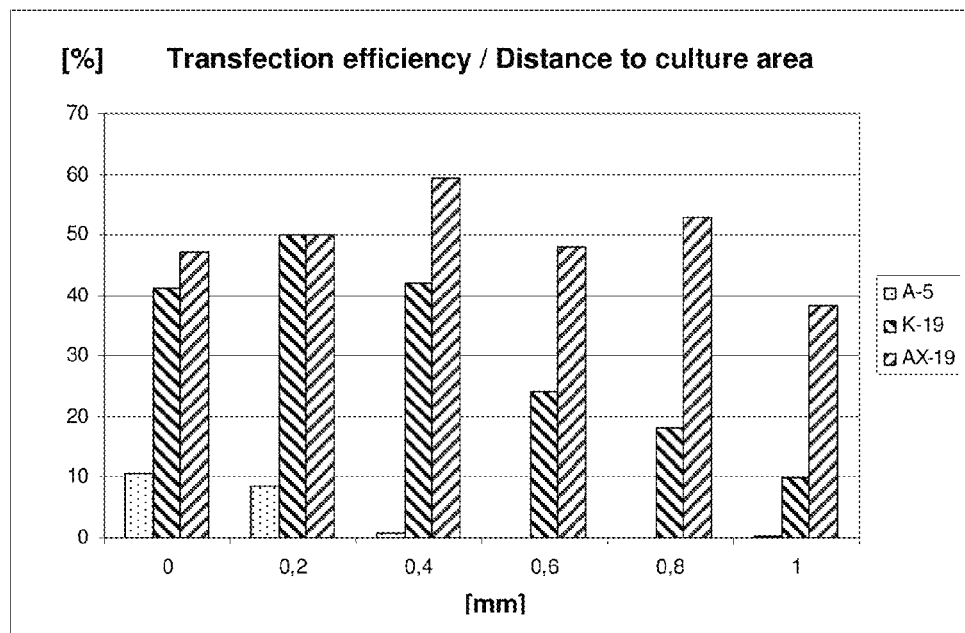
FIG. 8 shows in a bar diagram of the transfection efficiency as a function of the distance between the electrodes in an electrode arrangement according to the invention and the cells adhered on the culture area at three different high voltage pulses (x-axis: distance [mm], y-axis: transfection efficiency [%], A-5=weak voltage pulse, K-19=moderate voltage pulse, AX-19=high voltage pulse).

FIG. 8 shows the dependency of transfection efficiency on the distance of the electrodes between the cells to be treated with varying magnitude of voltage pulses respectively. Transfection means in this context the introduction of nucleic acid molecules (here DNA) into living cells by means of electrical voltage pulses. While at relatively high voltage (AX-19) there is an only poor dependency of the transfection efficiency on the distance between the electrodes and the cells, at low voltage (A-5) it is seen, that the transfection efficiency increases with decreasing distance between the electrodes and the cells. In contrast moderate voltage pulses (K-19) show an optimum at medium sized distances. It illustrates that the distance between the electrodes and the cells has a more or less great influence on the transfection efficiency depending on the strength of the voltage pulse.

LIST OF REFERENCE NUMBERS

1 Electrode arrangement
2 Electrodes
3 Inner space
4 Container
5 Bottom area
6 Space
10 Electrode arrangement
11 Isolating material
12 Electrodes
13 Inner space
14 Container
15 Bottom area
16 Area
17 Electrode arrangement
18 Electrodes
19 Isolating material
20 Electrode arrangement
21 Electrodes
22 Carrier
23 Base body
24 Border area
25 Underside
26 Isolating material
27 Spacer
28 Contact elements
29 Region
30 Upper side
31 End
32 Area
33 Face surface

The invention claimed is:
1. Electrode arrangement comprising:
an plane underside,
at least three electrodes,
electrically isolating material, wherein
each of said at least three electrodes
(i) is at least in part made of metal and/or an electrically conducting synthetic material, and

(ii) has an area which is disposed face to face with a corresponding area of the respective other electrode defining a space between said area and said corresponding area, wherein each of the spaces between the at least three electrodes is completely filled with the isolating material, and wherein said plane underside is defined by exposed surfaces of said at least three electrodes and said electrically isolating material.

2. The electrode arrangement according to claim 1, wherein the electrodes are formed like a plate or pin.

3. The electrode arrangement according to claim 1, wherein the areas are lateral surfaces of electrode plates that are disposed plane-parallel.

4. The electrode arrangement according to claim 1, wherein the isolating material is a thermoplastic polymer.

5. The electrode arrangement according to claim 1, wherein the electrode arrangement includes at least one spacer on at least one side facing adherent cells.

6. The electrode arrangement according to claim 1, wherein the electrode arrangement is configured for insertion into at least one container being at least partially filled with a liquid and wherein the isolating material displaces at least a part of the liquid upon insertion into the container.

7. The electrode arrangement according to claim 1, wherein the electrodes are at least partially disposed at the underside of a carrier.

8. The electrode arrangement according to claim 7, wherein the carrier is such that it can be configured to be inserted into or placed onto a reaction vessel so that the electrodes are exposed to an inner space of the reaction vessel.

9. The electrode arrangement according to claim 8, wherein the reaction vessel is part of a multiwell plate.

10. The electrode arrangement of claim 1, wherein the electrode arrangement is configured for an application of at least one electric field to adherent cells.

11. The electrode arrangement according to claim 1, wherein at least 4 electrodes are provided.

12. The electrode arrangement according to claim 6, wherein the at least one container has a bottom area to which living cells adhere.

13. The electrode arrangement according to claim 4, wherein the thermoplastic polymer is polyvinylchloride, polystyrene, polypropylene, polyethylene and/or polycarbonate.

14. The electrode arrangement according to claim 1, wherein at least 5 electrodes are provided.

15. The electrode arrangement according to claim 14, wherein 6-12 electrodes are provided.

16. Method for applying at least one electric field to adherent cells comprising
providing the electrode arrangement according to claim 1,
applying said at least one electric field to adherent cells, wherein said adherent cells are optionally electroporated and wherein the electrode arrangement is optionally in form of at least one dipping electrode device.

17. Method for applying at least one electric field to adherent cells comprising
generating the electric field by applying a voltage to at least two electrodes,
wherein the electric field is focused at a side of the electrodes facing the cells and/or is restricted to the space between the cells and the side of the electrodes facing the cells.

18. The method according to claim 17, wherein the electric field is restricted to the space between the cells and the exposed front side of the electrodes.

19. The method according to claim 17, wherein electrically isolating material is placed between the electrodes for focusing and/or restricting the electric field.

20. The method according to claim 17, wherein an exposed front side of the electrodes is inserted into at least one container having a bottom area to which the cells adhere.

21. The method according to claim 17, wherein the effect of the electric field on the cells is optimized by adjusting a distance between the cells and the electrodes.

* * * * *